United States Patent [19]

Chen

[11] Patent Number: 5,624,294
[45] Date of Patent: Apr. 29, 1997

[54] HUMDINGER, GEL SPINNER

[75] Inventor: John Y. Chen, Pacifica, Calif.

[73] Assignee: Applied Elastomerics, Inc., South San Francisco, Calif.

[21] Appl. No.: 152,734

[22] Filed: Nov. 15, 1993

Related U.S. Application Data

[63] Continuation-in-part of Ser. No. 114,688, Aug. 30, 1993, and a continuation-in-part of Ser. No. 935,540, Aug. 24, 1992, and a continuation-in-part of Ser. No. 876,118, Apr. 29, 1992, and a continuation-in-part of Ser. No. 705,096, May 23, 1991, and a continuation-in-part of Ser. No. 957,290, Oct. 6, 1992, and a continuation-in-part of Ser. No. 705,711, May 23, 1991, Pat. No. 5,262,468, which is a continuation-in-part of Ser. No. 211,426, Jun. 24, 1988, Pat. No. 5,153,254, which is a continuation-in-part of Ser. No. 921,752, Oct. 21, 1986, abandoned, which is a continuation-in-part of Ser. No. 572,172, Jan. 18, 1984, Pat. No. 4,618,213, which is a continuation-in-part of Ser. No. 458,703, Jan. 17, 1983, abandoned, which is a continuation-in-part of Ser. No. 134,977, Mar. 28, 1980, Pat. No. 4,369,284, which is a continuation-in-part of Ser. No. 916,731, Jun. 19, 1978, abandoned, which is a continuation-in-part of Ser. No. 815,315, Jul. 13, 1977, abandoned, which is a continuation-in-part of Ser. No. 778,343, Mar. 17, 1977, abandoned.

[51] Int. Cl.$^6$ ..................................................... A63H 1/32
[52] U.S. Cl. ............................................. 446/253; 446/486
[58] Field of Search ...................................... 446/253, 254, 446/486; 482/110, 121, 122

[56] References Cited

U.S. PATENT DOCUMENTS

| | | | |
|---|---|---|---|
| 342,264 | 5/1886 | Plimpton | 446/253 X |
| 2,988,846 | 6/1961 | Samuel | 446/253 |
| 3,069,162 | 12/1962 | Samuel | 446/253 X |
| 4,369,284 | 1/1983 | Chen | . |
| 4,618,213 | 10/1986 | Chen | . |

FOREIGN PATENT DOCUMENTS 1268431  1/1969  United Kingdom .

OTHER PUBLICATIONS

SC:1102–89 Shell Chemical Technical Bulletin "*KRATON® Thermoplastic Rubber in oil gels*" Apr. 1989.

Orbiter, Rainbow Products, Trail Oregon.

*Primary Examiner*—Mickey Yu

[57] ABSTRACT

Spinning twisting string toys herein referred to as "humdingers" are disclosed which comprises one or more gel bodies having two or more substantially parallel holes approximately equal distance apart extending through the gel body transversely along a selected axis of rotation. The parallel holes are treaded with a string which is twisted and untwisted alternatively by a pull and release action in play. The parallel holes may be surrounded by an reinforcing material interlocked with the gel body about the vicinity surrounding the holes or each of the parallel holes may be fitted with a tear resistant hollow tube insert for preventing cutting by the shear forces of the twisting string(s). In the operation of the humdingers, the gel body, the hollow tubes, and the string(s) are made in such a manner so that they do not result in disastrously effect caused by the extremely high centrifugal and shearing forces generated during play.

12 Claims, 3 Drawing Sheets

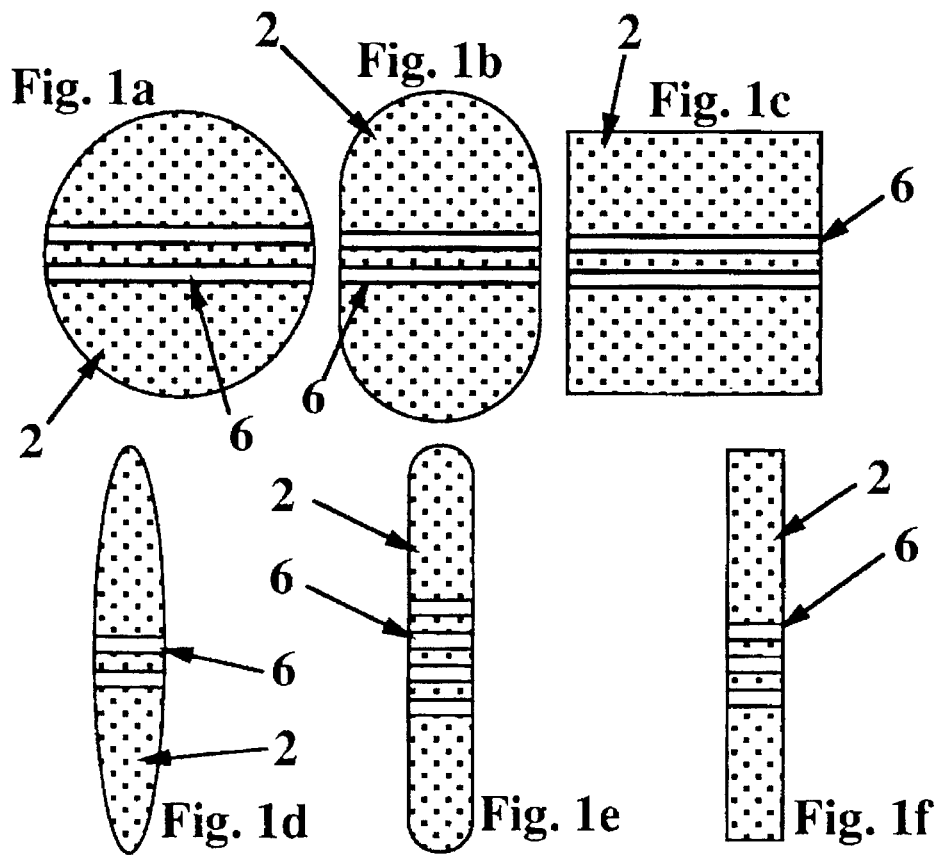
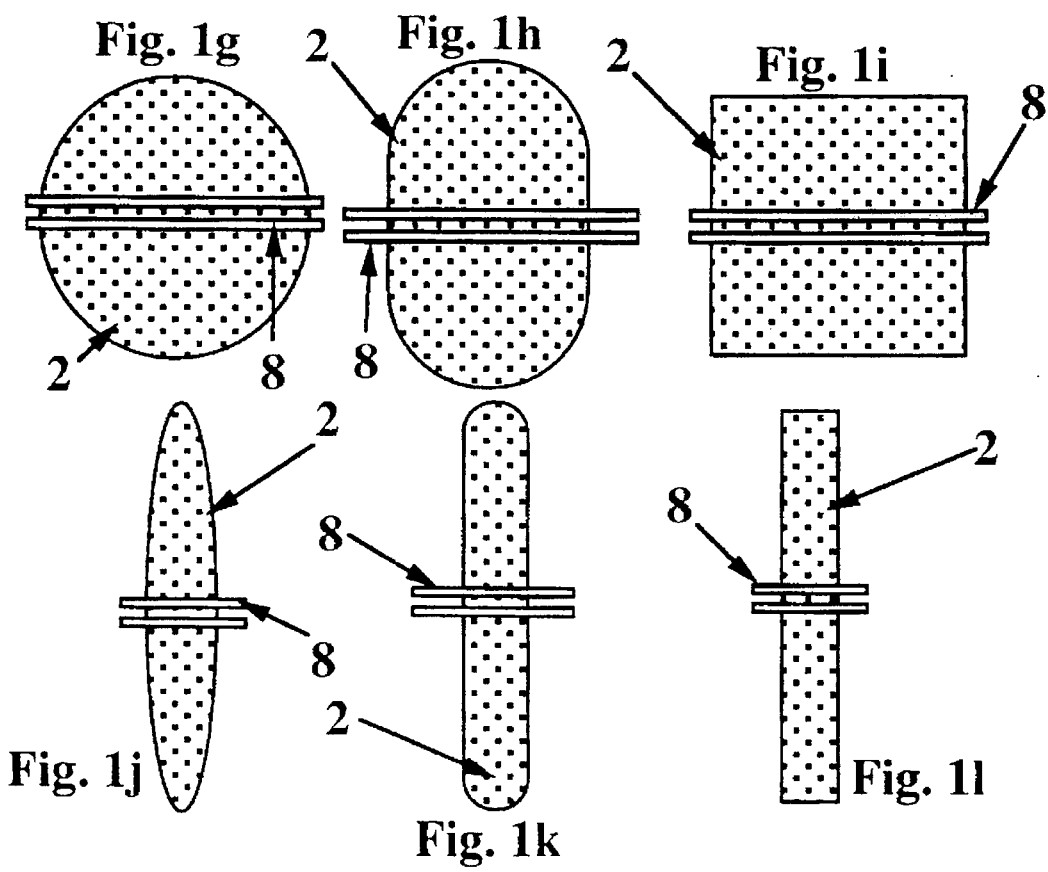

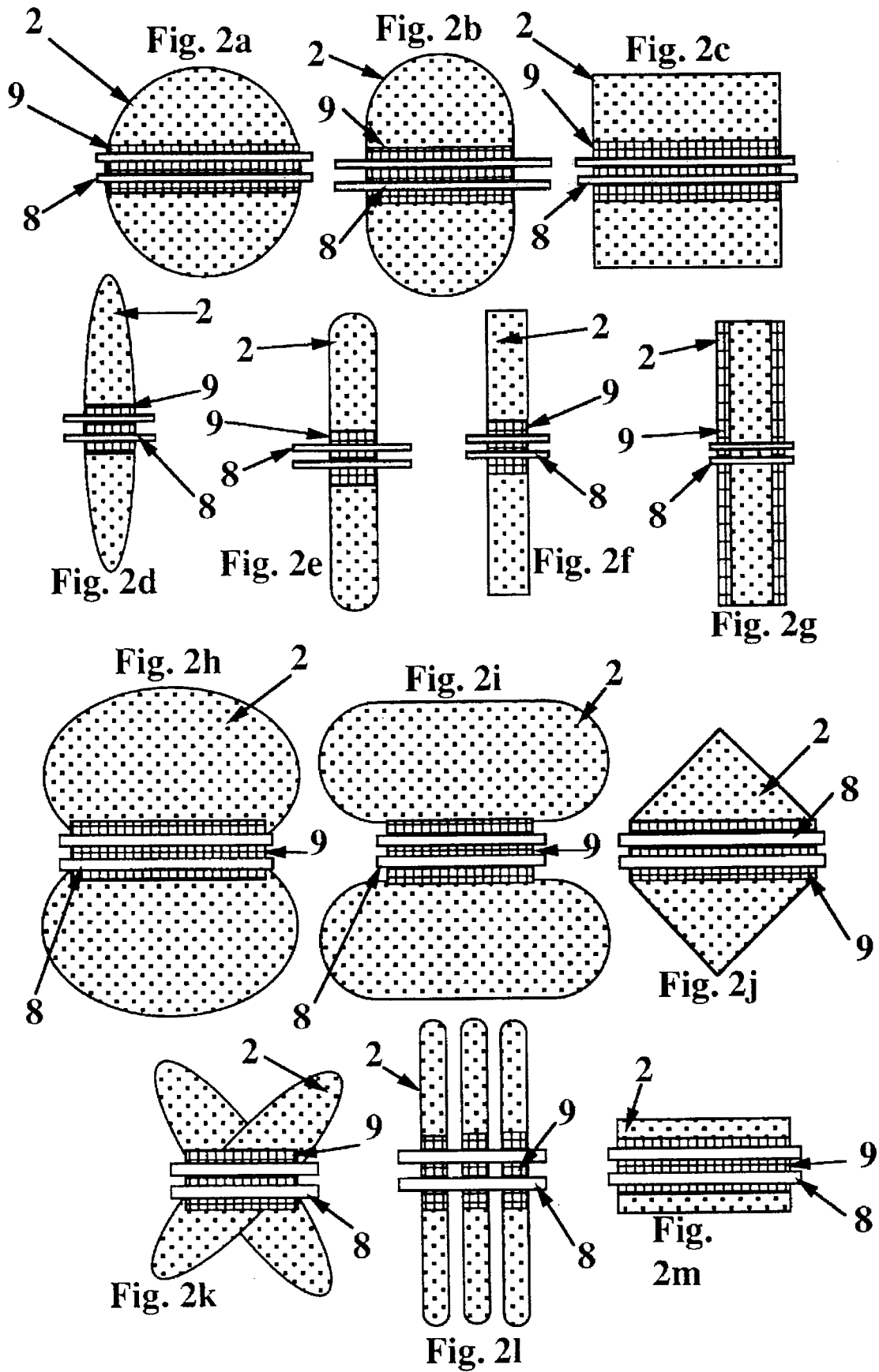

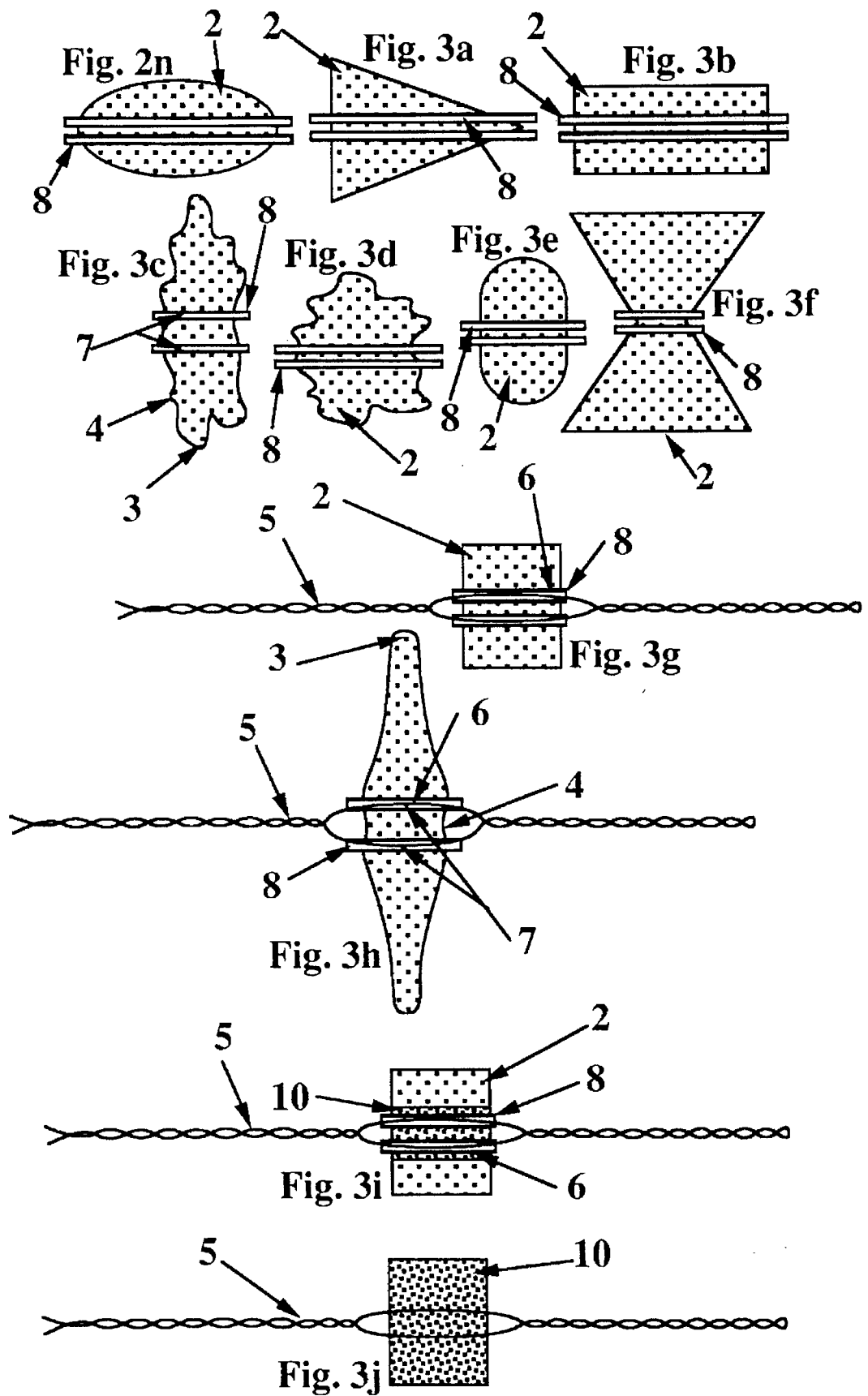

HUMDINGER, GEL SPINNER

REFERENCE TO RELATED APPLICATIONS AND PATENTS

This application is a continuation-in-part application of applications Ser. No. 114,688, filed Aug. 30, 1993; Ser. No. 935,540 filed Aug. 24, 1992; Ser. No. 876,118 filed Apr. 29, 1992; Ser. No. 705,096 filed May 23, 1991; Ser. No. 957,290 filed Oct. 6, 1992; and Ser. No. 705,711 filed May 23, 1991 now U.S. Pat. No. 5,262,468 which is a continuation-in-part application of Ser. No. 211,426 filed Jun. 24, 1988 and issued as U.S. Pat. No. 5,153,254 on Oct. 6, 1992 which is a continuation-in-part application of Ser. No. 921,752 filed Oct. 21, 1986 now abandoned which is a continuation-in-part of application Ser. No. 572,172, filed 18 Jan. 1984 and issued as U.S. Pat. No. 4,618,213 on 21 Oct. 1986, which is a continuation-in-part of application Ser. No. 458,703, filed 17 Jan. 1983, now abandoned which is a continuation-in-part of application Ser. No. 134,977, filed 28 Mar., 1980 and issued as U.S. Pat. No. 4,369,284 on 18 Jan. 1983, which in turn is a continuation-in-part of application Ser. No. 916,731, filed 19 Jun. 1978, now abandoned which is a continuation-in-part of application Ser. No. 815,315, filed 13 Jul. 1977, now abandoned which is a continuation-in-part of application Ser. No. 778,343, filed 17 Mar. 1977 now abandoned. The subject matter contained in the related applications and patents are specifically incorporated herein by reference.

FIELD AND BACKGROUND OF THE INVENTION

The present invention relates to certain spinning toys. A hand spinning toy which is very simple to make, requires only a simple disk and a string. The string is treaded through two small holes positioned about the center of the disk. The disk is set into continuous alternating rotating motion by pulling and then releasing the string while holding it in opposite directions which keeps it spinning.

In the eighteen century, large U. S. one-half pennies were commonly use by children for spinning on a string. A name was coined for spinning string toy, a "humdinger". The coins are immediately recognizable by their two small holes punched near their centers. Some coins may have three holes because they were initially miss-punched and off balanced or the first hole was punched too large. The word "humdinger" has since lost its meaning. Today, the word refers to anything that is extraordinary.

During the nineteen century, various rigid, hard, machinable materials 9 such as shells, wood, bones, metals, ceramics, ivory, glass, and certain plastics were used to make buttons. The holes on the large buttons made them ideal disks for spinning on a string.

SUMMARY OF THE INVENTION

I have unexpectedly discovered novel string spinning toys made from ultra-soft, ultra-elastic gel compositions. For want of a simpler name to call them, I will hereinafter define, describe, claim and in all respects refer to the novel untra-elastic gel spinning toys of my invention as "humdinger, gel spinners" or more simply, "humdingers".

One embodiment of the humdingers of the invention comprises: a highly elastic gel body having a selected shape, a selected volume, and a selected surface; said gel body being capable of elongated deformation by the action of centrifugal force of rotation on said shape, said volume and said surface of said gel body and an equal opposite action of an elastic force equal to the centrifugal force by said gel body; said gel body suspended on a selective length of string having two ends; said string treaded into said gel body at two adjacent entry points on said surface at about a selected, x, distance apart forming lines of said string substantially parallel to and approximately equal distance along a selected axis of rotation through said volume, and out of said gel body at two adjacent exit points at approximately said x distance apart on said surface substantially opposite the surface of said entry points; said string forming a string loop through said gel body and with said ends tied together to provide for alternatively twisting and untwisting of said string loop and the application of a variable torque by said string loop to said entry and said exit points and through said volume of said gel body about said selected axis of rotation and maintaining rotation of said gel body by the continue twisting and untwisting of said string loop; said torque being varied by a change in the separation of the distance of the lines of said string within said volume of said gel body cause by the centrifugal force of rotation.

A further embodiment of the humdingers of the invention comprises: a highly elastic gel body capable of exhibiting an elongated deformation by the action of centrifugal force of rotation and an equal and opposite action of an elastic force equal to the centrifugal force by said gel body; said gel body having two or more adjacent holes through said gel body positioned a selected, x, distance apart and substantially parallel to and approximately equal distance along a selected axis of rotation of said Gel body; said gel body suspended on a one or more string(s) treaded through said holes and with the ends of said string(s) tied together to provide for alternatively twisting and untwisting of said string(s) resulting in the application of a variable torque to said holes by said string(s) to said gel body about said axis of rotation and maintaining rotation of said gel body by the continue twisting and untwisting of said string(s); said torque being varied by a change in separation of the distance of said holes cause by the centrifugal force of rotation.

A still further embodiment of the humdingers of the invention comprises: a highly elastic gel body capable of exhibiting an elongated deformation by the action of centrifugal force of rotation and an equal and opposite action of an elastic force equal to the centrifugal force by said gel body; said gel body having two or more adjacent holes through said gel body positioned a selected, x, distance apart and substantially parallel to and approximately equal distance along a selected axis of rotation of said gel body; a selected length of two or more tear resistant tubes inserted into said holes and positioned within said gel body; said gel body suspended on a one or more string(s) treaded through said tubes and with the ends of said string(s) tied together to provide for alternatively twisting and untwisting of said string(s) resulting in the application of a variable torque by said string(s) to said tear resistant tubes by said string(s) to said gel body about said axis of rotation and maintaining rotation of said gel body by the continue twisting and untwisting of said string(s); said torque being varied by a change in separation of the distance of said holes cause by the centrifugal force of rotation.

Another embodiment of the humdingers of the invention comprises: a highly elastic gel body capable of exhibiting an elongated deformation by the action of centrifugal force of rotation and an equal and opposite action of an elastic force equal to the centrifugal force by said gel body; said gel body having two or more adjacent holes through said gel body positioned a selected, x, distance apart and substantially parallel to and approximately equal distance along a selected axis of rotation of said gel body; said gel body having a tear resistant reinforced interlocking material region surrounding said holes; said gel body suspended on a one or more string(s) treaded through said holes and with the ends of said string(s) tied together to provide for alternatively twisting and untwisting of said string(s) resulting in the application of a variable torque to said holes by said string(s) to said gel body about said axis of rotation and maintaining rotation of said gel body by the continue twisting and untwisting of said string(s); said torque being varied by a change in separation of the distance of said holes contained within said tear resistant reinforced interlocking material region cause by the centrifugal force of rotation.

A still another embodiment of the humdingers of the invention comprises: a highly elastic gel body capable of exhibiting an elongated deformation by the action of centrifugal force of rotation and an equal and opposite action of an elastic force equal to the centrifugal force by said gel body; said gel body having two or more adjacent holes through said gel body positioned a selected, x, distance apart and substantially parallel to and approximately equal distance along a selected axis of rotation of said gel body; said gel body having a tear resistant gel region surrounding said holes; said gel body suspended on a one or more string(s) treaded through said holes and with the ends of said string(s) tied together to provide for alternatively twisting and untwisting of said string(s) resulting in the application of a variable torque to said holes by said strings) to said gel body about said axis of rotation and maintaining rotation of said gel body by the continue twisting and untwisting of said string(s); said torque being varied by a change in separation of the distance of said holes contained within said tear resistant gel region cause by the centrifugal force of rotation.

In a still further embodiment of the humdingers of the invention, the gel bodies may be torqued about a selected axis of rotation by insertion of one or more flexible thin rods in place of the strings. Thin rods made of metal such as spring steel, piano wires, brass wire, copper, and the like would be suitable for such purpose. The gel bodies may also be casted, molded, or formed with one or more high tear resistant gel strips, gel rods, or gel handles serving the same purpose as the strings or rods for rotating the gel bodies.

In the operation of the humdingers, the gel body, the tubes, the string(s), the interlocking materials g surrounding the holes are designed, selected, and constructed in accordance with specific physical requirements and conditions so that they do not result in a disastrously effect caused by the extremely conditions of play.

The various aspects and advantages of the humdingers of the invention will become apparent to those skilled in the art upon consideration of the accompanying disclosure and the drawings.

DESCRIPTION OF THE DRAWINGS

FIG. 1a–1i Representative sectional views of humdingers of the invention.

FIG. 2a–2n Representative sectional views of more humdingers of the invention.

FIG. 3a–3j Representative sectional views of additional humdingers of the invention.

DESCRIPTION OF THE PREFERRED
EMBODIMENTS

The humdingers of the invention comprises one or more gel bodies 2; and each gel body 2 having two or more holes 6 substantially equal distance apart extending through the gel body 2 transversely along a selected axis of rotation of the gel body 2. The holes 6 are threaded through with a suitable string 5 forming a loop with the ends of the string 5 tied together which string(s) 5 are twisted and untwisted alternatively an play. The holes 6 may be surrounded by an reinforcing (tear resistant) interlocking material interlocked with the gel body 2 about the vicinity surrounding the holes 6 or each of the holes 6 of the gel body 2 may be fitted with (tear resistant) tubes 8 for preventing cutting by the tear forces of the twisting string(s) 5. Where the gel body 2 contains three or more holes 6, the corresponding numbers of strings 5 are threaded through each of the holes 6 and tied together at opposite ends. In the operation of the humdingers, the gel body 2, the tubes 8, and the string(s) 5 are made in such a manner so that they do not result in disastrously effects caused by the extreme conditions generated during play.

The dynamic variables of extreme centrifugal, elastic (high elongation), stress and shear forces, the extreme high torque, and the extreme accelerations and deaccelerations are ever changing during play. These variables if not properly considered in the design, selection of materials, and the gel bodies 2 construction may have drastic effects on the humdingers of the invention. A humdinger build without such considerations cannot synchronize under high rates of rotation. In order for the humdingers of the invention to operate in substantial synchrony and exhibit stability, the affects of these variables must be taken into account. Such effects produced by the dynamic variables include: instability, uncontrollable chaotic behavior, damping out of the driving force (pulling and releasing action), lack of synchronization, extreme sensitivity to initial conditions of play, fibrillations, and the like. Due to the highly elastic nature of the gel bodies 2, the gel bodies 2 are deformed by the centrifugal force as the rate of rotation is increased. The inherent disorder and instability associated with an elastic liquid are not encountered with rigid materials used in conventional string 5 spinning-disk toys. Therefore, the dynamic variable are of the utmost importance in considering the design of the instant humdingers. The humdingers of the present invention are designed in accordance with specific physical requirements.

The gel bodies 2 are not rigid bodies; but can be view as semi-elastic liquids. They are highly elastic and dynamically deformable under rotation (see FIGS. 3a deforms to 3h and 3d deforms to 3c). Since the gel bodies 2 are highly elastic, they are easily deformed under very low to moderate shear and stress forces. The gel bodies 2 are not suitable for use as rigid gyroscopes or flywheels which require high rigidity. The gel bodies 2 of the invention when rotated about an axis of rotation will experience increase deformation from its original shapes with increase rate of rotation (e.g. see FIG. 3c and 3h). The deformation of the gel bodies 2 of the invention under rotation is a non-uniform phenomena and is substantially independent of its original shape. Irrespective of the original shapes of the gel bodies 2, when subjected to rotational forces, the gel bodies 2 will deform in a highly elastic, predetermined, nonuniform, and nonradial manner. Because of the high deformations resulting from rotational forces, the gel bodies 2 will redistribute its mass outwardly by elongating perpendicularly with respect to its axis of rotation (see FIG. 3c and 3h). The gel material at the extreme outer parts 3 (equator) of the gel bodies 2 will experience greater and greater centrifugal force as the gel bodies 2 rotate and elongate more and more. The gel bodies 2 if not properly designed will be pulled apart by the increasing centrifugal force of rotation. For example, the centrifugal force of a rotating gel body 2 having a mass of about 50 grams and an elongated mass about the body's equator of about 10 centimeter may produce from about 50 to about 250 pound-force or higher.

The humdingers of the invention comprises one or more gel bodies 2 suspended on a inner looped string 5. The gel bodies 2 are made with two or more holes 6 parallel about their axis of rotation. The holes 6 are positioned approximately equal distance apart about the axis of rotation of the gel bodies 2 and may pass through the gel bodies' 2 center of mass, but at some distance, x, form it. gel bodies 2 may also be made with two or more holes 6 positioned parallel passing about a chosen axis of the radius of gyration but at some distance, x, from it. It is well known that, whereas, the center of mass is independent of any origin but dependent solely on the distribution of mass within an object, the radius of gyration depends directly upon the axis chosen for its calculation.

Viewed in another way, the holes 6 may also be positioned approximately equal distance apart about the axis of rotation of the gel bodies 2 and may pass through the gel bodies' 2 center of suspension (suspended from a line passing through its center of mass, i.e. at neutral equilibrium) but at some distance, x, form it. This is to say, one hole is placed above the center of mass line, the gel body 2 is in stable equilibrium; and the other hole is placed below the line, in unstable equilibrium. Such positioning of the holes 6 with respect to the center of mass (the center of weight) or the center of suspension will provide the desired torque need to maintain adequate rotation imparted by the twisting strings 5.

If the distance, x, is zero then the two holes 6 will superimpose upon one another and the torque applied by the treaded strings 5 when inserted through the holes 6 and twisted upon itself will also be zero. Therefore, a suitable separation distance, x, is needed to separate the holes 6 from each other and the holes 6 from the chosen axis of rotation. The holes 6 should be separated approximately equal distance from the axis of rotation. A suitable distance, x, may be selected based on various factors, including the moment of inertia, axis of rotation, and the necessary torque need to rotate the gel bodies 2 about its axis of rotation by the action of the twisting string 5. If the separations between the holes 6 with respect to the axis of rotation is slightly off, then the torque applied to the gel bodies 2 will be unbalanced. The unbalanced rotation would not be totally disastrous, but may produce a desirable off-balanced effect. While the humdinger may still adequately operate, it will be more difficult to keep the wobbling humdinger rotating in the unbalanced state.

As the gel bodies 2 rotate, the moment of inertia will change and the point of the applied torque will also change (see FIG. 3c/7 and FIG. 3h/7). The moment of inertia of the gel bodies 2 changes because the shape of the gel bodies 2 changes (e.g. FIG. 3. d' is transformed to c' and g' is transformed to h') with increase rate of rotation. Due to the ultra-elastic nature of the composition of the gel bodies 2, as their shape change, so will the position of the holes 6 with respect to each other and respect to their distances from the axis of rotation. Any off-centering of the placement of the holes 6 with respect to the axis of rotation will be greatly magnified by the centrifugal force acting on the gel body 2. The torque acting on the gel bodies 2 will greatly vary as the centrifugal force further separates the holes 6 from each other and from the axis of rotation (see FIG. 3, c'/4 and h'/4).

Moreover, the over all original shape of a gel body 2 will also affect the position of the holes 6 as the gel body 2 is set into rotation. The change in separations between the holes 6 and between the holes 6 and the axis of rotation due to the centrifugal force acting on the gel body 2 is also affected by the shape of the original gel body 2 as a whole. In other words, the configuration of the original shape of the gel body 2 directly affects the amount and direction of the deformation about the holes 6 caused by the centrifugal force. A stretching or deformation of one part of a gel body 2 will directly affect all other parts of the gel body 2. Therefore, any deformation by an applied force on any part of the gel body 2 will correspondingly cause deformation to the other parts of the gel body 2. The holes 6 and the shade of the gel bodies 2 are always in a state of flux due to the force of rotation. The holes 6 freely move about as the shape of the gel body 2 is changed by the force of rotation. This is the nature of gel bodies 2 (i.e. semi-elastic liquids) under dynamic motion as opposed to rigid bodies.

Suitable strings 5 suspending the gel bodies 2 may having a test strength ef at least greater one pound. strings 5 of sufficient test strengths of less than about 10, 15, 20, 25, 30 pounds and greater may be used depending on the size, weight, axis of rotation, and inertia of the gel bodies 2 and the rate of rotation. The string 5 is passed through the two holes 6 of a gel body 2 and tied into a loop. For gel bodies 2 having three or more holes 6, the individual strings 5 are passed through the holes 6 and tied together at opposite ends. The gel body 2 is set into continuous alternating rotating motion with an initial whirl. of the humdinger followed by alternately pulling and releasing the string 5 while holding it in opposite directions which keeps it spinning. Between the second and fourth full reversal of rotation of the gel body 2, the string 5 will had sufficient twist to tear off, cue into or through the gel material separating the holes 6. No gel material of sufficient strength can resist the tremendous shearing action of the twisting strings 5 between the holes 6. For example, 0.070 inch diameter string 5 with an approximately 0.30 square inch lateral surface area in contact with a 50 gram gel body 2 rotating at 500 to 900 rpm, the twisting shear force of the strings 5 may reach as from a low force of about 15 to a high of about 54 pound-force or higher. Therefore, to overcome the strings' 5 shearing force, it would be of advantage to surround the holes 6 with a high tear resistant gel 10 or with an reinforcing, interlocking material 9.

Suitable interlocking materials 9 for use in the humdingers of the invention include: open cell foams, other polymeric or elastomeric (Kraton) materials, porous materials, multi-layered coatings, single layered, composite layered materials. As an example, an opened cell foam when dipped into the instant composition will form an interpenetrating physical networks (interlocking of gel composition and foam).

Furthermore, the interlocking materials 9 surrounding the holes 6 of the gel bodies 2 may be made from flexible materials, such as fibers and fabrics of cotton, flax, and silk. Other flexible materials include: elastomers, fiber-reinforced composites, maohair, and wool. Useful synthetic fibers include: acetate, acrylic, aremid, glass, modacrylic polyethylene, nylon, olefin, polyester, rayon, spandex, carbon, sufar, polybenzimidazole, and combinations of the above. Useful open-cell plastics include: polyamides, polyimides, polyesters, polyisocyanurates, polyisocyanates, polyurethanes, poly (vinyl alcohol), etc. Open-celled Plastic (foams) suitable for use with the compositions of the invention are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference. These include: open and non-opened cell silicone, polyurethane, polyethylene, neoprene, polyvinyl chloride, polyimide, metal, ceramic, polyether, polyester, polystyrene, polypropylene. Example of such foams are: Thanol®, Arcol®, Ugipol®, Arcel®, Arpak®, Arpro®, Arsan®, Dylite®, Dytherm®, Styrofoam®, Trymet®, Dow ethafoam®, Ensolite®, Scotfoam®, Pyrell®, Volana®, Trocellen®, Minicel®, and the like.

Additionally, a preferred embodiment of the invention which would adequately resist the shearing force of the twisting string 5 (without any interlocking material ) is to provide a suitable length of tubing for insertion into the passage of the holes 6. Such a tube 8 may be made from a highly tear resilient tubing material (i.e. a material having high tear resistance). The tube 8 may be made from a rigid, flexible, or elastic material. The tube 8 may be smooth, treaded, ribbed, porous or roughly surfaced; it may be of any suitable hollow shape, round, square, rectangular, oval, and the like. The tubes 8 may be inserted into the holes 6 by hand. The length of the tube 8 should be sufficient to match the thickness portion of the gel body 2 which is being suspended by the string 5. The diameter of the tube 8 should be sufficient to receive the selected size of the string 5 passing through it without being too tight or too loose. A ribbed flange (not shown) may be incorporated (as a securing device) at the ends of the tube 8 to further secure the tube 8 within the holes 6 of the gel body 2. The securing device may also be constructed of a two coupled flanges (not shown) which inserts on to both tubes 8 at each ends keeping the separations of the holes 6 and tubes 8 am a fixed distance apart and securing the tubes 8 inside the holes 6 of the gel body 2 during the humdinger's operation. In this way the torque will be fixed and no longer variable.

Tubing material suitable for use in the present invention include such tear resistant materials as: tetrafluoerthylene, chlorotrifuoroethylene, polyvinylidene fluoride, high density polyethylene, polyvinyl chlorides, acrylonitrile butadiene styrene, chlorinated polyether, cellulose acetate butyrate, polypropylene, polycarbonate, polyphenylene oxide, phenolic plastics, rubbers plastics, polyester, neoprene rubber, nitrile rubber, certain silicone rubbers, chorosulfonated polyethylene, fluoroelatomers, polyvinyl chloride elastomers, wood, aluminum, polysulfide, and the like.

The shape of the gel bodies 2 of the humdingers of the invention may be of any suitable solid shape, such as a sphere, a hemisphere, a spherical triangle, a spherical segment, a spherical sector, a curved volume of a right cylinder, a curved volume of a right cone, an oblate spheroid, an oblate hemispheroid, a semi-hemispheroid, a quai-hemispheriod, a prolate, a spheroid, a prolated hemispheroid, a frustum of right circular cone, a solid lute, or an ellipsoid, and the like.

Other shapes of gel bodies 2 of the humdingers of the invention include: a cube, a rectangular solid, a parallelogram solid, a rhombus solid, a trapezoid solid, a general quadrilateral solid, a rectangular parallelepiped, a prism, a truncated triangular prism, a pyramid, a frustum of pyramid, a bifolium solid, an evolute solid, a lemniscate of Bernoeulli, two-leaved rose solid, a nephroid solid, a three-leaved rose curve solid, a four-leaved rose curve solid, an elliptic paraboloid, a hyperbolic paraboloid, a hyperboloid, a tetrahedron, an octahedron, an icosahedron, a dodecahedron, an ellipsoid, a spheroid, an oblate spheroid, or a prolate spheroid, and the like.

Any axis of the gel bodies 2 may be chosen as the axis of rotation. The gel bodies 2 may be of any suitable size, from less than 1 cubic centimeter to 20 cubic centimeter or greater.

In the operation of the humdingers of the invention, the string's 5 twisting action imparts rotation to the gel body 2 so as to elongate the gel body 2 during rotation. The elongated Gel body 2 will reach a maximum elongation due to centrifugal force of 50% or more. Elongations of 100%, 200%, 300%, 400%, 500%, 600%, 700% and higher are possible depending on the amount of tension of the pull of the humdinger's string 5. gel bodies 2 of of the invention can be designed to withstand elongations higher than 1,000% which can occur at extreme high rate of rotation.

The operation of the humdingers of the invention can be ready observed under strobe light. The number of revolutions per minute may be counted in this way. The changes in radius can be measured. The change in gel body 2 shape can be observed and measured. The centrifugal force acting on the rotating gel body 2 can be likewise determined at any instant of time, at any instant rate of rotation, at any instant change in gel body 2 shape. The perpendicular-axis elongation effect of the gel body 2 can be view under strobe light; its regions of deformation and redistributing of mass can be viewed, measured and ready determined by grid markings on the gel body 2.

The compositions making up the gel bodies 2 of the humdingers of the invention may be made from any gel material with suitable elastic properties. Gels described in patents and applications under "RELATED APPLICATIONS AND PATENTS", now sold under trademark Memory-Gel® (having gel rigidities of from about 100 gram Bloom to about 1,500 gram Bloom and higher) are especially advantageous and suitable for forming the gel bodies 2 of the invention. Gels less suitable and less advantageous for use include polymer gels, crosslink polymer gels, and the like. Other less suitable gels include high strength silicone gels, urethane gels, water gels, and the like. Such gels are inherently weak and do not make good gel bodies 2 by themselves; they can not withstand the centrifugal force generated during rotation. Weak gels can be enclosed by the stronger more advantageous gels described in the invention.

The gel bodies 2 of humdingers of the invention made with tear resistant gel 10 are characterized by a gel rigidity of at least above about 300 gram Bloom; while, the gel bodies 2 of humdinger made with tear resistant tubes are characterized by a gel rigidity of at least above about 80 gram Bloom; and gel bodies 2 utilizing tear resistant reinforced interlocking materials are characterized by a gel rigidity of at least above about 80 gram Bloom. Finally, the compositions of of tear resistant gels surrounding the holes 6 of the gel bodies 2 are characterized by a gel rigidity of at least above about 300 gram Bloom.

Gels especially suitable for use in making gel bodies 2 of the invention can be prepared by melt blending an admixture consisting essentially of: (A) 100 parts by weight of a high viscosity triblock copolymer of the general configuration polystyrene- ethylene-butylene-styrene) where said triblock copolymer is characterized as having a Brookfield Viscosity of a 20 weight percent solids solution of said triblock copolymer in toluene at 25° C. of about 1,800 cps and higher. (B) from about 200 to about 1,300 parts by weight of an plasticizing oil.

The most desirable and advantages compositions forming the gel bodies 2 of the invention are high viscosity triblock copolymers which have the more general configuration A-B-A wherein each A is a crystalline polymer end block segment of polystyrene; and B is a elastomeric polymer center block segment of poly(ethylenebutylene). The poly (ethylene-butylene) and polystyrene portions are incompatible and form a two-phase system consisting of sub-micron domains of glassy polystyrene interconnected by flexible poly(ethylene-butylene) chains. These domains serve to crosslink and reinforce the structure. This physical elastomeric network structure is reversible, and heating the polymer above the softening point of polystyrene temporarily disrupt the structure, which can be restored by lowering the temperature. Most recent reviews of triblock copolymers are found in the "*ENCYCLOPEDIA OF POLYMER SCIENCE AND ENGINEERING*", Volume 2 and 5, 1987–1988; "Thermoplastic Elastomers", MODERN PLASTIC ENCYCLOPEDIA, 1989; and Walker, B. M., Ed. et al., *HANDBOOK OF THERMOPLASTIC ELASTOMERS*, Van Nostrand Reinhold Co., 2nd Edition, 1988. There publications are incorporated herein by reference).

Less typically, the Brookfield Viscosity values of (A) can range from about 1,800 cps to about 30,000 cps or higher. The proportion of hydrocarbon plasticizing oil in (B) is more Preferably from about 250 to about 1,200 parts per 100 parts of the triblock copolymer.

The high viscosity triblock copolymer of the invention can have a broad range of styrene end block to ethylene and butylene center block ratio of approximately about 20:80 or less to about 40:60 or higher. Examples of high viscosity triblock copolymers that can be utilized to achieve one or more of the novel properties of the present invention are styrene-ethylene-butylene-styrene block copolymers (SEBS) available from Shell Chemical Company and Pecten Chemical Company (divisions of Shell Oil Company) under trade designations Kraton G 1651, Kraton G 1654X, Kraton G 4600, Kraton G 4609 and the like. Other grades of (SEBS) polymers can also be utilized in the present invention provided such SEBS polymers exhibits the required high viscosity. Such SEBS polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C.

The styrene to ethylene and butylene weight ratios for these Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values. Shell Technical Bulletin SC: 1393-92 gives solution viscosity as measured with a Brookfield model RVT viscometer at 25° C. for Kragon G 1654X at 10% weight in toluene of approximately 400 cps and at 15% weight in toluene of approximately 5,600 cps.

The styrene to ethylene and butylene weight ratio of SEBS useful in forming the gel bodies 2 can range from lower than about 20:80 to above about 40:60. More specifically, the values can be 19:81, 20:80, 21:79, 22:78, 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and higher. Other ratio values of less than 19:81 or higher than 51:49 are also possible. Broadly, the styrene end block to ethylene and butylene center block ratio of the triblock copolymers of the invention is about 20:80 to about 40:60, less broadly about 31:69 to about 40:60, preferably about 32:68 to about 38:62, more preferably about 32:68 to about 36:64, particularly more preferably about 32:68 to about 34:66, especially more preferably about 33:67 to about 36:64, and most preferably about 33:67. In accordance with the present invention, triblock copolymers such as Kraton G 1654X having ratios of 31:69 or higher can be used and do exhibit some very similar physical properties in many respects to Kraton G 1651 while Kraton G 1654X with ratios below 31:69 may also be use, but they are less preferred due to their decrease in the desirable properties of the final composition. Various triblock copolymers of the compositions forming the humdingers of the invention can be blended so as to produce a blend of varying ratios of triblock copolymers of the gel composition as desired.

Minor amounts of other polymers and copolymers can be melt blended with the styrene-ethylene-butylene-styrene block copolymers mentioned above without substantially decreasing the desired properties. Such polymers may also be utilized in one or more regions of the Gel bodies 2 of the invention; these include (SBS) styrene-butadiene-styrene block copolymers, (SIS) styrene-isoprene-styrene block copolymers, (low styrene content SEBS) styrene-ethylene-butylene-styrene block copolymers, (SEP) styrene-ethylene-propylene block copolymers, $(SB)_n$ styrene-butadiend and $(SEB)_n$, $(SEBS)_n$, $(SEp)_n$, $(SI)_n$ styrene-isoprene multi-arm, branched, and star shaped copolymers and the like. Still, other homopolymers can be utilized in minor amounts; these include: polystyrene, polybutylene, polyethylene, polypropoyene and the like. The above less desirable block copolymers can also be utilized by themselves with an appropriate amount of plastizer for making the gel bodies 2 of the invention, but are less desirable because of their inherent property limitations.

Plasticizers particularly preferred for use in practicing the present invention are will known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight. Many such oils are known and commercially available. Examples of representative commercially oils include Amoco® polybutenes, hydrogenated polybutenes and polybutenes with epoxide functionality at one end of the polybutene polymer: Example of such polybutenes include: L-14 (320 $M_n$), L-50 (420 $M_n$), L-100 (460 $M_n$), H-15 (560 $M_n$), H-25 (610 $M_n$), H-35 (660 $M_n$), H-50 (750 $M_n$), H-100 (920 $M_n$), $_H$300 (1290 $M_n$), L-14E (27–37 cst @ 100° F. Viscosity), H-300E (635–690 cst @ 210° F. Viscosity), Actipot E6 (365 $M_n$), E16 (973 $M_n$), E23 (1433 $M_n$) and the like. Example of various commercially oils include: ARCO Prime (55, 70, 90, 200, 350, 400 and the like), Duraprime and Tufflo oils, other white mineral oils include: Bayol, Bernoi, American, Blandol, Drakeol, Ervol, Gloria, Kaydol, hitetek, Lyondell (Duraprime 55, 70, 90, 200, 350, 400, etc), Marcol, Parol, Peneteck, Primol, Protol, Sontex, and the like.

The high viscosity triblock copolymer component by itself lacks the desired properties; whereas, when the triblock copolymer (having Brookfield Viscosities of a 20 weight percent solids solution in toluene at 25° C. of about 1,800 cps or higher and styrene to ethylene and butylene ratio preferably of the range contemplated in the instant invention) is combined with selected plasticizing oils with an average molecular weight preferably of about 200 to about 700, as determined by ebulliscopic methods, wherein, for most purposes, the oil constitutes about 200 to about 1,300 Darts and especially more preferably about 250 to about 900 parts by weight of the triblock copolymer, that a soft and highly elastic material is obtained. This transformation of the triblock copolymer structure in heated oil resulting in a composition having a gel rigidity preferably of about 100 gram or lower to about 1,500 gram Bloom and substantially without oil bleedout along with high tensile strength and elongation and other desirable combination of physical properties is unexpected. As used herein, the term "gel rigidity" in gram Bloom is determined by the gram weight required to depress a gel a distance of 4 mm with a piston having a cross-sectional area of 1 square centimeter 23° C.

in accordance with the practice of the present invention, the aforementioned molecular weight range plasticizing oils are most preferred. Generally, plasticizing oils with average molecular weights less than about 200 and greater than about 700 may also be used (e.g. H-300 (1290 Mn).

The composition utilized for the gel bodies 2 can also contain useful amounts of conventionally employed additives such as stabilizers, antioxidants, antiblocking agents, colorants, fragrances, flame retardants, other polymers in minor amounts and the like to an extend not affecting or substantially decreasing the desired properties of the present invention.

Additives useful in the composition of the present invention include: tetrakis[methylene 3,-(3'5'-di-tertbutyl-4"-hydroxyphenyl) propionate]methane, octadecyl 3-(3",5"-di-tert-butyl-4"-hydroxyphenyl) propionate, distearyl-Pentaerythritol-diproprionate, thiodiethylene bis- (3,5-ter-butyl-4-hydroxy) hydrocinnamate, (1,3, 5-trimethyl-2,4,6-tris [3,5-di-tert-butyl-4-hydroxybenzyl]benzene) , 4,4"-methylenebis (2,6-di-tert-butylphenol) , steraric acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, waxes (e.g. polyethylene, polypropylene, microcrystalline, carnauba, paraffin, montan, candelilla, beeswax, ozokerite, ceresine, and the like). Minor amounts of other polymers and copolymers can be melt blended with the styrene-ethylene-butylene-styrene block copolymers mentioned above without substantially decreasing the desired properties. Such polymers include (SBS) styrene-butadiene-styrene block copolymers, (SIS) styrene-isoprene-styrene block copolymers, (low styrene content SEBS) styrene-ethylene-butylene-styrene block copolymers, (SEP) styrene-ethylene-propylene block copolymers, (SB)n styrene-butadiene and (SEB)n, (SEBS)n, (SEP)n, (SIS)n styrene-isoprene multi-arm, branched, and star shaped copolymers and the like. Still, other homopolymers can be utilized in minor amounts; these include: polystyrene, polybutylene, polyethylene, polypropylene and the like.

The composition can also contain metallic pigments (aluminum and brass flakes), $TiO_2$, mica, fluorescent dyes and pigments, phosphorescent pigments, aluminatrihydrate, antimony oxide, iron oxides ($Fe_3O_4$, -$Fe_2O_3$, etc.), iron cobalt oxides, chromium dioxide, iron, barium ferrite, strontium ferrite and other magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. The report of the committee on *Magnetic Materials*, Publication NMAB-426, National Academy Press (1985) is incorporated herein by reference.

The gel compositions of the present invention may be prepared in accordance with the methods disclosed in U.S. Pat. No. 5,239,723 and other related applications and patents referred to above (which is herein incorporated by reference).

The gel compositions forming the humdingers of the invention can also contain gases as an additive, i.e. the gel composition can be foamed. Foam is herein defined as tightly or loosely packing aggregation of gas bubbles, separated from each other by thin or thick layers of gel composition. Many types of foamed gel compositions (from ultra high density to ultra low density) can be produced as desired by (i) adding gas to the molten gel composition during processing, and (ii) producing gas in the molten gel composition during processing. Gas can be added by whipping a gas into the molten gel composition before it cools or introduce a gas into the molten gel composition and then expand or reduce the size of the gas bubbles by reducing the pressure to reduce the bubbles size or applying high pressure to expand the bubbles size. In this regard, inert gases such as Carbon dioxide, Nitrogen, Helium, Neon, Argon, Krypton, Xenon and Radon are suitable. Air can also be used. Gas can be produced in the molten gel composition by adding one or more of a "blowing agent" to the composition. Useful blowing agents include dinitroso compounds, such as dinitroso pentamethylene-tetramine, azodicarbonamide, 4,4' oxybis (benzenesulfonyl) hydrazine, 5-phenyltetrazole, p-toluenesulfonyl semicarbazide, sulfonyl hydrazide, such as benzene sulfonylhydrazide. Water can be used as a "blowing agent" to produce varying density of foam gel compositions; water used to advantage can be in the form of mist, droplets, steam, and hot or cold water. The density of the foam gel compositions can vary from less than 1.00 kilograms per cubic meter to near the solid gel composition density.

The basis of the gel compositions forming the novel gel bodies 2 of this invention resides in the fact that a high viscosity poly(styrene-ethylene-butylene-styrene) triblock copolymer having styrene end block to ethylene and butylene center block ratio preferably within the contemplated range of from about 20:80 to about 40:60, more preferably from between about 31:69 to about 40:60 when blended in the melt with an appropriate amount of plasticizing oil makes possible the attainment of gel elastomer compositions having a desirable combination of physical and mechanical properties, notably high elongation at break of at least 1000%, tensile strength of about at least $8 \times 10^5$ dyne/$cm^2$ and higher, low elongation set at break of substantially not greater than about 2%, tear resistance of at least $5 \times 10^5$ dyne/$cm^2$ and higher, substantially about 100% snap back when extended to 1,000% elongation, and a gel rigidity of substantially from about 100 gram Bloom to about 1,500 gram Bloom. It should be noted that when the ratio falls below 31:69, various properties such as elongation, tensile strength, tear resistance and the like can decrease while retaining other desired properties, such as gel rigidity, flexibility, elastic memory.

A gel of about 800 to 1,500 gram Bloom and higher are sufficiently suited as a tear resistant gel 10 (i.e., resistant to the cutting actions of the twisting string) for use in surrounding the holes 6 of the gel bodies 2. Such high tear resistant gels 10 are prepared by melt blending an admixture consisting essentially of: (A) 100 parts by weight of a high viscosity triblock copolymer of the general configuration poly(styrene- ethylene-butylene-styrene) where said triblock copolymer is characterized as having a Brookfield Viscosity of a 20 weight percent solids solution of said triblock copolymer in toluene at 25° C. of about 1,800 cps and higher. (B) from about 200 to about 600 parts by weight of plasticizing oil. The resulting higher tear resistant gel 10 will have sufficient resistance for protecting the holes of the gel bodies 2. Less preferably, the gels with rigidities of about 300 to about 1,500 gram Bloom and higher are suitable for use as gel bodies 2 without any additional need for any reinforcing, interlocking material 9 or tube 8 to protect the holes against cutting by the twisting string. With respect to gel bodies made from gel compositions having rigidities in the range of about 750 to about 1,500 and higher, these are especially preferred for use as humdingers of the invention.

The instant gel bodies 2 formed from the compositions have various additional important advantages in that they do not crack, creep, tear, crack, or rupture in flextural, tension, compression, or other deforming conditions of normal use; but rather the molded Gel bodies 2 made from the instant composition possess the intrinsic properties of elastic memory enabling the gel bodies 2 to recover and retain its original molded shape after many extreme deformation cycles. In applications where low rigidity, high elongation, good compression set and excellent tensile strength are important, the instant compositions would be preferred.

The holes 6 of the gel bodies 2 may be preformed by molding, casting, or any manner of forming the gel bodies 2. Gels of one or more higher tear resistance may be utilized to surround the holes 6 of the gel bodies 2, while lower gel rigidities may be use to advantage for the outer portion of the gel bodies 2 surrounding the holes 6. For example, a first high tear resistant gel 10 of rigidity of about 300 to about 1,500 gram Bloom may be used to cast the central portion of the gel body 2 forming the holes 6 and a second gel of about 100 to 500 gram Bloom or lower may be used to mold the portion of the gel body 2 surrounding the holes 6. The holes 6 may be punched, cut, or pierced using a knitting needle. With respect to gel bodies 2 made from higher tear resistant gels 10, the string may be treaded through the gel body 2 by simply piercing and tying the ends of the string and it is then ready for play. A knitting needle if properly driven into the gel and withdrawn will leave very little trace of its penetration into the gel body 2. Two or more holes 6 may also be driven into the gel body 2 by insertion of the tubes 8. In forming the holes 6, the holes 6 should be properly aligned substantially parallel and spaced apart about the selected axis along the line of the center of mass. The preformed holes 6 in the gel body 2 may be made small enough to provide a tight fit for the tubes 8. The preformed holes 6 may be made small enough or suitably channeled inside with ribs or contours to provide a substantial tight fit around the tubes 8. Likewise, the gel bodies 2 may be casted with the tubes 8 in place.

The invention is further illustrated by means of the following illustrative embodiments, which are given for purpose of illustration only and are not meant to limit the invention to the particular components and amounts disclosed.

EXAMPLE I

A comparison was made between a low viscosity poly (styrene-ethylene-butylene-styrene) triblock copolymer having styrene end block to ethylene and butylene center block ratio below the range between 31:69 to 40:60 and a high viscosity Poly(styrene-ethylene-butylene-styrene) triblock copolymer of the invention. Three different triblock copolymers were melt blended separately with a paraffinic white petroleum oil. Table I below shows the physical properties obtain with respect to each of the different viscosity and styrene to ethylene and butylene ratio triblock copolymer oil-blends tested.

The properties were measured as follows: Tear Propagation (ASTM D 19938 modified), Cracking (ASTM D 518 Method B modified), Tensile Strength (ASTM D 412 modified), Ultimate elongation (ASTM D 412 modified), Tensile Set (ASTM D 412 Modified), Compression Sen (ASTM D 395 modified), Snap Back, and Hand Kneading (60 seconds).

TABLE I

| | | | | |
|---|---|---|---|---|
| SEBS[2] | 28:72 | 100 | | |
| SEBS[3] | 29:71 | | 100 | |
| SEBS[4] | 33:67 | | | 100 |
| Paraffinic oil[5] | | 400 | 400 | 400 |
| Stabilizer[6] | | 2.5 | 2.5 | 2.5 |
| Breaking strength[7], dyne/cm$^2$ | $4 \times 10^5$ | $4 \times 10^5$ | $4 \times 10^6$ | |
| Tear propagation[8], dyne/cm$^2$ | $8 \times 10^4$ | $7 \times 10^4$ | $1 \times 10^6$ | |
| Compression set[10] at 24 hours | 81% (R) | 77% (R) | 0.0% | |
| Rigidity, gram Bloom | 1,536 | 1,520 | 360 | |

[1] Styrene to ethylene and butylene ratio
[2] Shell Kraton G1650 having a Brookfield viscosity of 1,500 cps as measured for a 20% weight solids solution in toluene at 25° C.
[3] Shell Kraton G 1652 having a Brookfield viscosity of 550 cps as measured for a 20% weight solids solution in toluene at 25° C.
[4] Shell Kraton G 1651 having a Brookfield viscosity of 2,000 cps as measured for a 20% weight solids solution in toluene at 25° C.
[5] ARCO prime 200,
[6] Irganox 1010,
[7] ASTM D 412 modified,
[8] ASTM D 1938 modified,
[9] ASTM D 412 modified,
[10] ASTM D 2395 modified,
Rruptured completely The results of Table I show drastically unacceptable poor properties of low viscosity triblock copolymers having styrene to ethylene and butylene ratios which are below the contemplated range of the instant invention.

EXAMPLE II

One hundred parts by weight of a high viscosity poly (styrene-ethylene- butylene-styrene) triblock copolymer (Shell Kraton G 1651) having a styrene end block to ethylene and butylene center block ratio of about 33:67 with 0.1 parts by weight of a stabilizer (Irrganox 1010) was melt blended with various quantities of a naphthenic oil (ARCO Tuffio 6024). Samples having the dimensions of 5 cm×5 cm×3 cm were cut and measured for gel rigidity on a modified Bloom gelometer as determined by the gram weight required to depress the gel a distance of 4 mm with a piston having a cross-sectional area of 1 cm$^2$. The average gel rigidity values with respect to various oil concentrations are set forth in Table II below.

TABLE II

| Oil per 100 parts of Triblock copolymer | gel Rigidity, gram Bloom |
|---|---|
| 360 | 500 |
| 463 | 348 |
| 520 | 280 |
| 615 | 240 |
| 635 | 220 |

TABLE II-continued

| Oil per 100 parts of Triblock copolymer | gel Rigidity, gram Bloom |
|---|---|
| 710 | 172 |
| 838 | 135 |
| 1,587 | 54 |

EXAMPLE III

Example II was repeated except about 980 parts oil was used and the gel rigidity found to about 101 Gram Bloom. Other properties measured were: tensile strength at break about $4.4 \times 10^6$ dyne/cm2, elongation at break about 2.4470%, elasticity modulus about $3.5 \times 10^4$ dyne/cm2, and shear modulus about $3.7 \times 10^4$ dyne/cm2. The tensile strength, elongation, elasticity modulus were measured with crosshead separation speed of 25 cm/minute at room temperature. The shear modulus was measured with a 1, 2, and 3 kilogram load at room temperature.

EXAMPLE IV

Example II was repeated except about 520 parts of a polybutene (Amocco Indopol H-300) was used and the gel rigidity found to be about substantially unchanged with respect to use of naphthenic oil alone.

EXAMPLE V

Example II was repeated except about 520 parts of a polybutene (Amoco C-60) was used and the gel rigidity found to be about substantially unchanged with respect to use of naphthenic oil alone.

EXAMPLE VI

Example II was repeated except about 520 parts of a polyterpene (Hercules Piccolyte S10) was used and the gel rigidity found to be about substantially unchanged with respect to use of naphthenic oil alone.

EXAMPLE VII

Example II was repeated except about 360 parts of a combined mixture of: 72 parts of a paraffinic oil (ARCO prime 200), 72 parts of a naphthenic oil (ARCO Tufflo 6014), 72 parts of a polybutene oligomer (Amoco Indopol H-200), 72 parts of a polypropene oligomer (Amoco Polypropene C-60), and 72 parts of a polyterpene oligomer (Hercules Piccolyte S10) was used and the gel rigidity found to be about substantially unchanged with respect to the use of naphthenic oil alone.

EXAMPLE VIII

Example III was repeated except 933 parts oil with 147 parts by weight of a high viscosity poly(styrene-ethylene-butylene-styrene) triblock copolymer containing 47 parts of a naphthenic process oil (Shell Kraton G 4609) having a styrene to ethylene and butylene ratio of about 33:67 was used and the physical properties were found to be about substantially unchanged with respect to the components used in Example III.

EXAMPLE IX

Example III was repeated except 933 parts oil with 147 parts by weight of a high viscosity poly(styrene-ethylene-butylene-styrene) triblock copolymer containing 47 parts of a paraffinic white petroleum oil (Shell Kraton G 4609) having a styrene to ethylene and butylene ratio of about 33:67 was used and the physical properties were found to be about substantially unchanged with respect to the components used in Example I.

EXAMPLE X

Example II was repeated except about 400 parts of oil was used and the properties measured were: tear propagation about $1.4 \times 10^6$ dyne/cm$^2$, no crack growth in 180° bend under 50 gram load for 5,000 hours at room temperature, tensile strength about $4 \times 10^6$ dyne/cm$^2$, elongation at break about 1,700%, tensile set about 0% at 1,200% elongation, compression set about 0% when tested under 5,000 gram load for 24 hours, and 100 snap back recovery after extension to 1,200%.

Examples XI–XIV-j below illustrate other modes of practice contemplated.

EXAMPLE XI

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 32:68 and the gel rigidity is found to be within the range of about 20 to about 800 gram Bloom.

EXAMPLE XII

The procedure of Example II is repeated and a poly (styrene-ethylene-butylene- styrene) triblock copolymer (characterized by a Brookfield Viscosity of a 20 weight percent solids solution in toluene at 25° C. of at least about 1,800 cps.) is used having a styrene end block to ethylene and butylene center block ratio of about 34:66 and the gel rigidity is found to be within the range of about 20 to about 800 gram Bloom.

EXAMPLE XIII

The procedure of Example II is repeated and a poly (styrene-ethylene-butylene- styrene) triblock copolymer (characterized by a Brookfield Viscosity of a 20 weight percent solids solution in toluene at 25° C. of at least about 1,800 cps.) is used having a styrene end block to ethylene and butylene center block ratio of about 36:64 and the gel rigidity is found to be within the range of about 20 to about 800 gram Bloom.

EXAMPLE XIV

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 38:62 and the gel rigidity is found to be within the range of about 20 to about 800 gram Bloom.

EXAMPLE XIV-a

The procedure of Example II is repeated and a poly (styrene-ethylene-butylene- styrene) triblock copolymer (characterized by a Brookfield Viscosity of a 20 weight percent solids solution in toluene at 25° C. of at least about 1,800 cps.) is used having a styrene end block to ethylene and butylene center block ratio of about 31:69 and the gel rigidity is found to be within the range of about 10 to about 800 gram Bloom.

EXAMPLE XIV-b

The procedure of Example II is repeated and a poly (styrene-ethylene-butylene- styrene) triblock copolymer (characterized by a Brookfield Viscosity of a 20 weight percent solids solution in toluene at 25° C. of at least about 1,800 cps.) is used having a styrene end block to ethylene and butylene center block ratio of about 37:63 and the gel rigidity is found to be within the range of about 10 to about 800 gram Bloom.

EXAMPLE XIV-c

The procedure of Example II is repeated and a poly (styrene-ethylene-butylene- styrene) triblock copolymer (characterized by a Brookfield Viscosity of a 20 weight percent solids solution in toluene at 25° C. of at least about 1,800 cps.) is used having a styrene end block to ethylene and butylene center block ratio of about 19:81 and the gel rigidity is found to be within the range of about 10 to about 800 gram Bloom.

EXAMPLE XIV-d

The procedure of Example II is repeated and a poly (styrene-ethylene-butylene- styrene) triblock copolymer (characterized by a Brookfield Viscosity of a 20 weight percent solids solution in toluene at 25° C. of at least about 1,800 cps.) is used having a styrene end block to ethylene and butylene center block ratio of about 20:80 and the gel rigidity is found to be within the range of about 10 to about 800 gram Bloom.

EXAMPLE XIV-e

The procedure of Example II is repeated and a poly (styrene-ethylene-butylene- styrene) triblock copolymer (characterized by a Brookfield Viscosity of a 20 weight percent solids solution in toluene at 25° C. of at least about 1,800 cps.) is used having a styrene end block to ethylene and butylene center block ratio of about 38:62 and the get rigidity is found to be within the range of about 10 to about 800 gram Bloom.

EXAMPLE XIV-f

The procedure of Example II is repeated and a poly (styrene-ethylene-butylene- styrene) triblock copolymer (characterized by a Brookfield Viscosity of a 20 weight percent solids solution in toluene at 25° C. of at least about 1,800 cps.) is used having a styrene end block to ethylene and butylene center block ratio of about 29:71 and the gel rigidity is found to be within the range of about 10 to about 800 gram Bloom.

EXAMPLE XIV-g

The procedure of Example II is repeated and a poly (styrene-ethylene-butylene- styrene) triblock copolymer (characterized by a Brookfield Viscosity of a 20 weight percent solids solution in toluene at 25° C. of at least about 1,800 cps.) is used having a styrene end block to ethylene and butylene center block ratio of about 26:74 and the gel rigidity is found to be within the range of about 10 to about 800 gram Bloom.

EXAMPLE XIV-h

The procedure of Example II is repeated and a poly (styrene-ethylene-butylene- styrene) triblock copolymer (characterized by a Brookfield Viscosity of a 20 weight percent solids solution in toluene at 25° C. of at least about 1,800 cps.) is used having a styrene end block to ethylene and butylene center block ratio of about 22:78 and the gel rigidity is found to be within the range of about 10 to about 800 gram Bloom.

EXAMPLE-XIV-i

The procedure of Example II is repeated and a poly (styrene-ethylene-butylene- styrene) triblock copolymer (characterized by a Brookfield Viscosity of a 20 weight percent solids solution in toluene at 25° C. of at least about 1,800 cps.) is used having a styrene end block to ethylene and butylene center block ratio of about 25:75 and the gel rigidity is found to be within the range of about 10 to about 800 gram Bloom.

EXAMPLE XIV-j

The procedure of Example II is repeated and a poly (styrene-ethylene-butylene- styrene) triblock copolymer (characterized by a Brookfield Viscosity of a 20 weight percent solids solution in toluene at 25° C. of at least about 1,800 cps.) is used having a styrene end block to ethylene and butylene center block ratio of about 26:74 and the gel rigidity is found to be within the range of about 10 to about 800 gram Bloom.

EXAMPLE XV

Example II is repeated except the molten composition is casted onto a polyether, a polyester, a surlyn ionomer open cell sponge thereby displacing the air space within the sponge and the gel rigidity is found to be greater than about the sum of the combined rigidity of the composition and sponge alone.

EXAMPLE XVI

The composition of Example II is casted unto a SCOT-FOAM® ⅛" thick: 5, 10, 15, 20, 25, 30, 35, 40, 45, 50, 60, 70, 80, 90, 100, and 200 ppi foam.

EXAMPLE XVII

Solid elastic gel bodies (having rigidities in the range of about 200 to about 1,000 gram Bloom) are molded in the form of a cube, a rectangular solid, a rectangular parallelepiped, a prism, a tetrahedron, an octahedron, a spheroid, an oblate spheroid, or a prolate spheroid, a curved volume of a right cylinder, a curved volume of a right cone, an oblate spheroid, an oblate hemispheroid, a semi-hemispheroid, a quai-hemispheriod, a prolate, a spheroid, and a prolated hemispheroid, two small diameter flexible urethane tubes are inserted into each solid parallel along an axis passing through the center of mass of the elastic solid gel bodies, the tubes are cut to the desired length, a string is treaded through the two tubes of each gel body to form a loop and tied together at the ends. The elastic gel solid bodies are use for spinning while suspended about the middle of the strings.

EXAMPLE XVIII

Solid elastic gel bodies (having rigidities in the range of about 600 to about 1,500 gram Bloom) are molded in the form of a cube, a rectangular solid, a rectangular parallelepiped, a prism, a tetrahedron, an octahedron, a spheroid, an oblate spheroid, or a prolate spheroid, a curved volume of a right cylinder, a curved volume of a right cone, an oblate spheroid, an oblate hemispheroid, a semi-hemispheroid, a quai-hemisphenod, a prolate, a spheroid, and a prolated hemispheroid, a string is treaded parallel along an axis passing through the center of mass of each gel body to form a loop and tied together at the ends. The elastic gel solid bodies are use for spinning while suspended about the middle of the strings.

While certain features of this invention have been described in detail with respect to various embodiments thereof, it will, of course, be apparent that other modifications can be made within the spirit and scope of this invention, and it is not intended to limit the invention to the exact details shown above except insofar as they are defined in the following claims.

I claim is:

1. A rotating string toy, which comprises a variable torque humdinger including:
   (a) a highly elastic gel body having
   (b) a selected shape,
   (c) a selected volume, and
   (d) a selected surface; said gel body being capable of elongated deformation by the action of centrifugal force of rotation on said shape, said volume and said surface of said gel body and
   (e) an equal opposite action of
   (f) an elastic force equal to the centrifugal force by said gel body; said gel body suspended on
   (g) a selective length of string having
   (h) two ends; said string threaded into said gel body at
   (i) two adjacent entry points on said surface at about
   (j) a selected, x, distance apart forming string lines substantially parallel to and approximately equal distance along
   (k) a selected axis of rotation through said volume, and out of said gel body at
   (l) two adjacent exit points at approximately said x distance apart on said surface substantially opposite the surface of said entry points; said string forming
   (m) a string loop through said gel body and with said ends tied together to provide for alternatively twisting and untwisting of said string loop and the application of
   (n) a variable torque by said string loop to said entry and said exit points and through said volume of said gel body about said selected axis of rotation and maintaining rotation of said gel body by the continue twisting and untwisting of said string loop; said torque being varied by a change in the separation of the distance of said string lines within said volume of said gel body cause by the centrifugal force of rotation;
   (o) said gel body having a gel rigidity of at least 80 gram Bloom; and
   (p) said gel body capable of withstanding an elongation of at least 50% during spinning.

2. A rotating string toy, which comprises a variable torque humdinger including:
   (a) a highly elastic, tear resistant gel body capable of exhibiting an elongated deformation by the action of centrifugal force of rotation and an equal and opposite action of an elastic force equal to the centrifugal force by said gel body: said gel body having
   (b) two or more adjacent holes through said gel body positioned
   (c) a selected, x, distance apart and substantially parallel to and approximately equal distance along
   (d) a selected axis of rotation of said gel body; said gel body suspended on
   (g) a one or more string(s) threaded through said holes and with the ends of said string(s) tied together to provide for alternatively twisting and untwisting of said string (s) resulting in the application of
   (f) a variable torque to said holes by said string(s) to said gel body about said axis of rotation and maintaining rotation of said gel body by the continue twisting and untwisting of said string(s) said torque being varied by a change in separation of the distance of said holes cause by the centrifugal force of rotation;
   (g) said gel body having a gel rigidity of at least 80 gram Bloom; and
   (h) said gel body capable of withstanding an elongation of at least 50% during spinning.

3. A rotating string toy, which comprises a variable torque humdinger including:
   (a) a highly elastic gel body capable of exhibiting an elongated deformation by the action of centrifugal force of rotation and an equal and opposite action of an elastic force equal to the centrifugal force by said gel body; said gel body having
   (b) two or more adjacent holes through said gel body positioned
   (c) a selected, x, distance apart and substantially parallel to and approximately equal distance along
   (d) a selected axis of rotation of said gel body;
   (e) a selected length of two or more tear resistant tubes inserted into said holes and positioned within said gel body; said gel body suspended on
   (g) a one or more string(s) threaded through said tubes and with the ends of said string(s) tied together to provide for alternatively twisting and untwisting of said string (s) resulting in the application of
   (f) a variable torque by said string(s) to said tear resistant tubes by said string(s) to said gel body about said axis of rotation and maintaining rotation of said gel body by the continue twisting and untwisting of said string(s); said torque being varied by a change in separation of the distance of said holes cause by the centrifugal force of rotation; and
   (g) said gel body capable of withstanding an elongation of at least 50% during spinning.

4. A rotating string toy, which comprises a variable torque humdinger including:
   (a) a highly elastic gel body capable of exhibiting an elongated deformation by the action of centrifugal force of rotation and an equal and opposite action of an elastic force equal to the centrifugal force by said gel body; said gel body having
   (b) two or more adjacent holes through said gel body positioned
   (c) a selected, x, distance apart and substantially parallel to and approximately equal distance along
   (d) a selected axis of rotation of said gel body; said gel body having
   (e) a tear resistant reinforced interlocking material region surrounding said holes; said gel body suspended on
   (f) a one or more string(s) threaded through said holes and with the ends of said string(s) tied together to provide for alternatively twisting and untwisting of said string (s) resulting in the application of (g) a variable torque to said holes by said string(s) to said gel body about said axis of rotation and maintaining rotation of said gel body by the continue twisting and untwisting of said string(s); said torque being varied by a change in separation of the distance of said boles contained within said tear resistant reinforced interlocking material region cause by the centrifugal force of rotation; and (h) said gel body capable of withstanding an elongation of at least 50% during spinning.

5. A rotating string toy, which comprises a variable torque humdinger including:

a) a highly elastic gel body capable of exhibiting an elongated deformation by the action of centrifugal force of rotation and an equal and opposite action of an elastic force equal to the centrifugal force by said gel body; said gel body having (b) two or more adjacent holes through said gel body positioned (c) a selected, x, distance apart and substantially parallel to and approximately equal distance along (d) a selected axis of rotation of said gel body; said gel body having (e) a tear resistant gel region surrounding said holes; said gel body suspended on (f) a one or more string(s) threaded through said holes and with the ends of said string(s) tied together to provide for alternatively twisting and untwisting of said string (s) resulting in the application of (g) a variable torque to said holes by said string(s) to said gel body about said axis of rotation and maintaining rotation of said gel body by the continue twisting and untwisting of said string(s); said torque being varied by a change in separation of the distance of said holes contained within said tear resistant gel region cause by the centrifugal force of rotation; and (h) said gel body capable of withstanding an elongation of at least 50% during spinning.

6. A rotating string toy of claim 1 or 2 wherein said gel body is made from a composition having a gel rigidity of at least 300 gram Bloom.

7. A rotating string toy of claim 3 or 4 wherein said gel body is made from a gel composition having a gel rigidity of at least 80 gram Bloom.

8. A rotating string toy of claim 5 wherein said gel body is made from a gel composition having a gel rigidity of at least above about 80 gram Bloom and said tear resistant gel region is made from a gel composition having a gel rigidity of at least 300 gram Bloom.

9. A rotating string toy, which comprises a variable torque humdinger including:

(a) a highly elastic solid gel body capable of exhibiting an elongated deformation by the action of centrifugal force of rotation and an equal and opposite action of an elastic force of to the centrifugal force by said gel body;

(b) means for applying a torque about a selected axis of rotation of said gel body so as to produce alternate rotation of said gel body about said axis and maintaining rotation of said gel body by said means so as to cause said elongated deformation by the centrifugal force of rotation; and (c) said gel body capable of withstanding an elongation of at least 50% during spinning.

10. A rotating toy, comprising:

(a) a highly elastic solid gel body;

(b) said gel body capable of withstanding an elongation of at least 50% during spinning;

(c) a string threaded through at least two points about a selected axis of rotation of said gel body to form a loop; and optionally, said gel body comprising (c) one or more of a shear resistant means through said points about said selected axis of rotation correspondingly surrounding said string through said gel body.

11. A rotating toy, comprising:

(a) an elastic solid gel body;

(b) a string through at least two points about a selected axis of rotation of said gel body to form a loop; and (c) said gel body capable of withstand an elongation of at least 50% during spinning.

12. A rotating toy, comprising:

(a) an elastic solid gel body;

(b) one or more strings threaded through at least two points about a selected axis of rotation of said solid gel body to form a loop; and (c) said gel body capable of withstanding an elongation of at least 50% during spinning.

* * * * *